US00PP07878P

United States Patent [19]

Griffith

[11] Patent Number: Plant 7,878

[45] Date of Patent: Jun. 2, 1992

[54] APPLE TREE NAMED GRIFFSPUR

[76] Inventor: Ralph B. Griffith, 203 Bainbridge St., Cobden, Ill. 62920

[21] Appl. No.: 571,445

[22] Filed: Aug. 23, 1990

[51] Int. Cl.[5] ..... A01H 5/00

[52] U.S. Cl. ..... Plt./34

[58] Field of Search ..... Plt./36

[56] References Cited

PUBLICATIONS

Anon., "Late-Maturing, Smooth Golden Apple with Superb, Rich Flavor", *Stark Bro's Fruit Tree Catalog & Guide for the Professional Grower,* copyright 1989, Stark Bro's Nurseries and Orchards Co., Louisiana, Mo., 63353, p. 15.

*Primary Examiner*—James R. Feyrer

[57] ABSTRACT

A new and distinct spur-type apple variety is provided which originated as a limb of the Griffith cultivar of U.S. Plant Pat. No. 2,835. The new variety consistently produces its fruit on short fruiting branches (spurs) which are shorter and much more abundant than the spurs of the Griffith cultivar.

2 Drawing Sheets

BACKGROUND OF THE INVENTION

This invention is directed to a new apple tree variety discovered as a single limb mutation of the Griffith apple variety. The Griffith variety is described and claimed in U.S. Plant Pat. No. 2,835, which patent is hereby incorporated by reference. The patented parent Griffith variety is being marketed under the Blushing Golden trademark by Stark Bro's Nurseries & Orchards Company of Louisiana, Mo. The source of the present new variety was a mutant limb borne on a Griffith apple tree which was located in an orchard owned by the originator in Union County, Ill. Specifically, the tree was located at Pt. S.E. S.W. Section 17, Range 1 W. 39.55 Acres, Road Dist. 1A, Union County, Ill.

The patented parent Griffith variety was described in U.S. Plant Pat. No. 2,835 as including the following distinguishing features:

(1) A general resemblance of the fruit in shape, size and flavor to the fruit of "Golden Delicious", but which develops an earlier yellow ground color and acquires a distinctive and attractive pink to red blush;

(2) A later fruit maturity of about 10 days latter than the fruit of "Golden Delicious";

(3) A longer keeping quality of the fruit;

(4) A waxy appearance of the fruit skin which does not develop russet, and absence of any tendency of the fruit to shrivel in normal storage as does the fruit of "Golden Delicious";

(5) Good resistance to spray injury; and (6) A richer and more acid flavor of the fruit than the fruit of "Golden Delicious."

The present new variety has been observed to exhibit various features distinct from those of the parent variety. The mutant limb of the parent tree was observed to have branches which bore fewer lateral shoots than other limb on the tree. It was further noted that the mutant limbs were producing fruit buds on short fruiting spurs with greater frequency than other limbs. Two-year-old branches produced 12 to 15 fruiting spurs per linear foot in contrast to 9 to 11 fruiting spurs per linear foot of the parent tree. The fruit appeared as if roped or braided along the long branch axes. In addition, the percentage of axiarlly buds which broke dormancy on the spur-type limb was distinctly higher than the percentage of buds which broke dormancy on typical limbs of the Griffith variety. The fruit bud and bud break counts are approximately 30% greater than in the parent variety.

After observing the spur-type characteristics of the a typical limb for several growing seasons, the originator propagated two second generation trees of the limb sport by grafting shoots from the mutant limb to Red Delicious seedling roots which were then planted in the originator's home orchard located at 203 Bainbridge Street, Cobden, Ill. 69620. The spur-type limb growth has been found to be a characteristic of all limb growth of these second generation trees. The trees display a strong tendency to produce abundant spurs along the axis of primary, secondary, and tertiary branches. While the propensity to form scaffold branching is about equal in the parent tree and the sport tree of this application, the sport branch angles appear to be appreciably wider than those of the parent, and assume angles of about 45 degrees. No supplemental support is required to support the fruit load in normal years. The new variety of apple has thus been observed to be a spur limb variant of the Griffith variety and has been named "Griffspur."

BRIEF DESCRIPTION OF THE PHOTOGRAPHS

DETAILED DESCRIPTION OF THE NEW VARIETY

Figure 1:
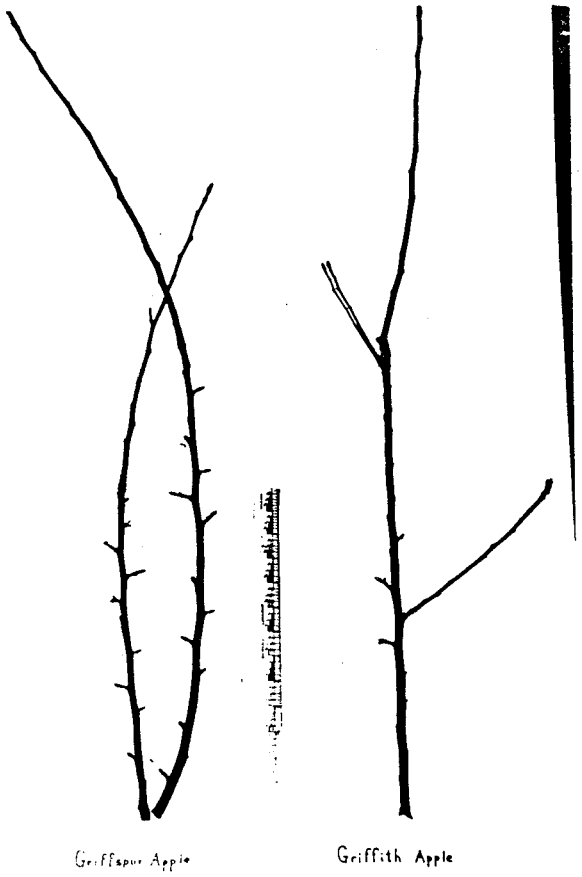
FIG. 1 is a photograph of a typical specimen of two year-old shoots of the parent (Griffith) variety (left) and a specimen of two year-old shoots of the present (Griffspur) variety (right).
Figure 2:
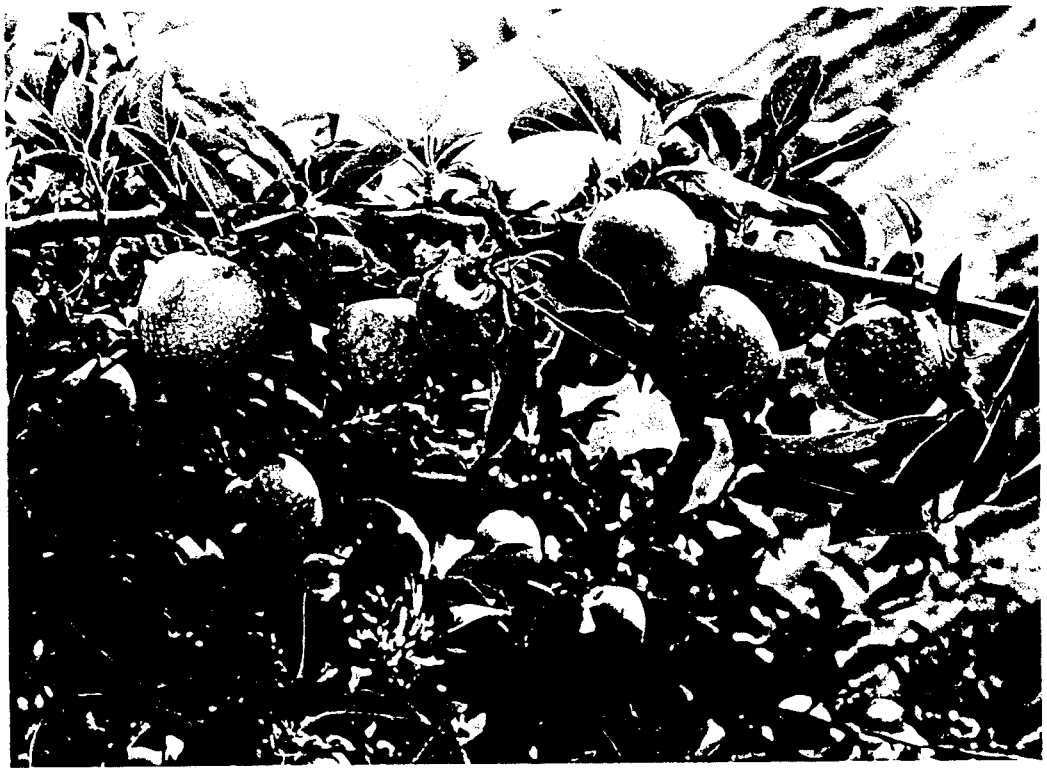
FIG. 2 is a photograph of a limb of mature apples of the present Griffspur variety.

The following is a detailed description of the new variety in which color terminology is to be accorded its ordinary dictionary significance except where otherwise indicated. The specimens described were grown in Cobden, Ill.

Dates of the first and last pickings: October 1 and October 6, respectively.

Tree: Medium size; moderately vigorous; upright and spreading; round-topped; moderately rapid growing; hardy; very productive; regular bearer.

*Trunk.*—Medium stocky; smooth.

*Branches.*—Medium thickness; smooth; spur-type branching. Color — Olive Brown, Plate XL, Color No. 17'', tone M of Ridgway's Color Standards and Nomenclature (hereinafter "Ridgway").

*Lenticels.*—Numerous; small.

*Leaves.*—Medium large size; medium width; medium length; ovate; taper-pointed; medium thickness; slightly rugose. Average length — from 4¼ inches to 4½ inches. Average width — from 2⅛ inches to 2¼ inches. Upper surface color — Dirk Cress Green, Plate XXXI, Color No. 29'', tone M (Ridgway). Under surface color — Lettuce Green, Plate V, Color No. 29, tone k (Ridgway).

Flowers: Late-mid bloom season, medium size, light pink.

Fruit:

*Spurs.*—Fat and clubbed; more than 30% greater number per linear foot than occur in the parent tree.

*Maturity when described.*—Hard ripe.

*Size.*—Uniform. Axial diameter — 3 inches. Transverse diameter — 2¾ inches.

*Form.*—Truncate at base; oval.

*Cavity.*—Symmetrical; rounded at base; acute; undulate; pubescent toward apex. Depth — ¾ inch. Breadth — 1 inch. Markings — russeted. Color — Tawny Olive, Plate XXXIX, Color No. 17'', tone i (Ridgway).

*Basin.*—Symmetrical; wide flaring base, undulate, glabrous. Depth — 5/16 inch. Breadth — ⅞ inch. Markings — none.

*Stem.*—Clubbed; medium slender; pubescent. Length — from ¾ to 1 inch. Breadth — 1/16 inch. Markings — russetted.

*Calyx.*—Closed; segments persistent; narrowly lanceolkate; acute; about ¼ inch long; approximate; converged from base toward center; pubescent on both inner and outer surfaces.

*Skin.*—Thick; medium tough; glossy; waxed. Dots — obscure; many; small; even; ruptured; circular. Color of dots — Maize Yellow, Plate IV, Color No. 19, tone f (Ridgway). Distribution of dots — uniform, except few near basin and cavity. Ground color — Citron Yellow, Plate XVI, Color No. 28, tone b (Ridgway). Color of markings — blushed; bright. Scarlet Red, Plate I, Color No. 3 (Ridgway). Bloom — lacking. Scarfskin — lacking. General color effect — yellow with red blush. When grown under the same conditions, with the same exposure to light, fruit skin colors of the parent and sport trees are indistinguishable.

*Flesh.*—Juicy. Color — satiny white with yellowish tint. Texture — firm; fine; crisp. Flavor — subacid; rich. Aroma — distinct. Quality — best.

*Core.*—Median. Bundle area — small; narrowly ovate; symmetrical at base; acute at base. Halves of core — equal. Bundles — inconspicuous. Bundle color — yellowish tinged. Core lines — clasping; indistinct in cross section. Carpellary area — indistinct; small. Calyx tube — glabrous toward base; apex narrowly cone-shaped; entire depth — 1 inch. Styles — present; united toward base; pubescent toward base. Stamens — in one basal whorl. Seed cells — axile; closed. Cell walls — distant; thin; tough. Length — ¾ inch. Breadth — ¼ inch. Longitudinal section — orbicular, obtuse at apex. Surface — fissured; tufted.

Seeds:

*Average number.*—5 or 6 perfect, and 2 or 3 imperfect.

*Number in one cell.*—2.

*Length.*—⅜ inch.

*Breadth.*—3/16 inch.

*Form.*—Obtuse.

*Color.*—Chocolate, Plate XXVIII, Color No. 7'', tone M (Ridgway).

Use: Market; dessert; excellent.

Keeping Quality: Excellent; about 210 days in ordinary storage.

Resistance to insects: Medium.

Resistance to disease: Medium.

Less time is expended in training and pruning the sport tree when compared to the parent tree, since the branches of the new tree 'Griffspur' are shorter and stronger than those of the parent tree. More thinning is required for the sport tree than of the parent tree, because of a higher level of flowering and fruit set.

'Griffspur' should be cross-pollinated for good fruit set. It blooms fairly slowly, 10 days longer than 'Golden Delicious', for example, which is advantageous when late frosts occur. 'Red Delicious' is a good pollinator for the early blossoms, and 'Jonathan' and 'Golden Delicious' are suitable as late pollinators.

I claim:

1. A new and distinct variety of apple tree substantially as illustrated and described, particularly characterized by a general resemblance of the fruit in shape, size, and flavor to the fruit of "Golden Delicious" but which develops an earlier yellow ground color and acquires a distinctive red blush, which has a fruit maturity of about 10 days later than the fruit of "Golden Delicious" and a longer keeping quality of the fruit, and when has good resistance to spray injury and a richer and more acid flavor than "Golden Delicious," the variety further characterized by more abundant, shorter spur-type fruiting branches than its parent variety described in U.S. Plant Pat. No. 2,835.

* * * * *